United States Patent [19]

Tabakoff

[11] Patent Number: 4,770,996

[45] Date of Patent: Sep. 13, 1988

[54] IDENTIFICATION OF INDIVIDUALS PREDISPOSED TOWARD ALCOHOL ABUSE

[76] Inventor: Boris Tabakoff, 2952 S. Haven Dr., Annapolis, Md. 21401

[21] Appl. No.: 873,514

[22] Filed: Jun. 12, 1986

[51] Int. Cl.⁴ .............................................. C12Q 1/34
[52] U.S. Cl. ...................................... 435/18; 435/19; 435/21; 435/25
[58] Field of Search ........................ 435/18, 21, 25, 19

[56] References Cited

PUBLICATIONS

Sullivan et al.–Chem. Abst., vol. 19, (1979), p. 3556a.

Primary Examiner—Sam Rosen
Attorney, Agent, or Firm—Dressler, Goldsmith, Shore, Sutker & Milnamow, Ltd.

[57] ABSTRACT

A method and an assay for ascertaining individuals likely to be predisposed to alcohol abuse is disclosed. The contemplated method ascertains the relative adenylate cyclase and monoamine oxidase activities of blood platelets and includes the steps of isolating platelets from the blood of an individual, assaying the isolated platelets for adenylate cyclase and monoamine oxidase activities, and comparing the observed activities.

11 Claims, 1 Drawing Sheet

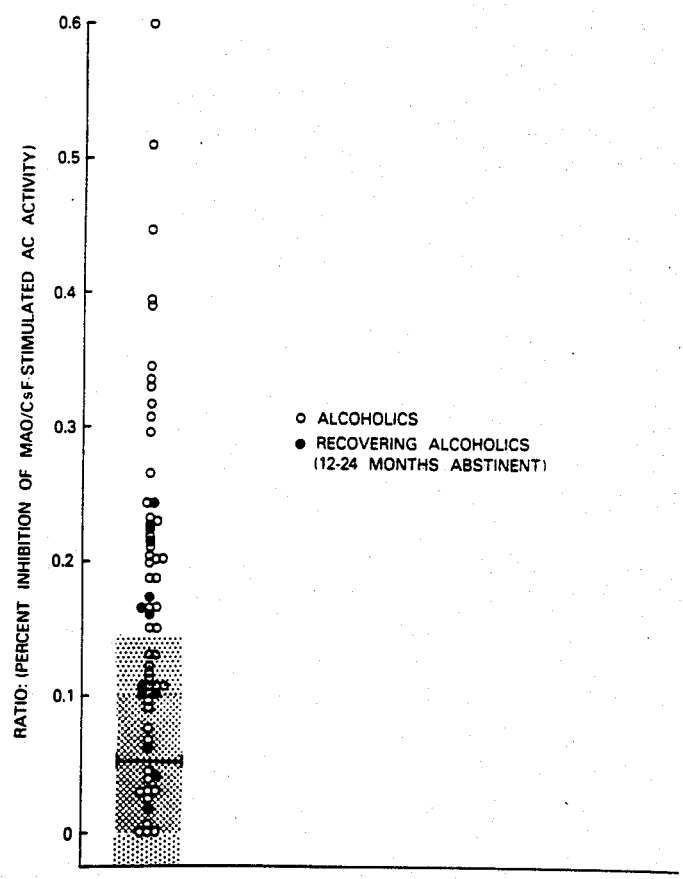

IDENTIFICATION OF INDIVIDUALS PREDISPOSED TOWARD ALCOHOL ABUSE

TECHNICAL FIELD

The present invention relates to clinical assays and in particular to assays related to identification of individuals predisposed toward alcoholism.

BACKGROUND

Health and medical costs related to alcohol abuse are staggering. In 1977, approximately twenty-eight billion dollars was expended for the care of patients with alcohol-related problems; this figure does not reflect the approximately twenty billion dollars of lost productivity that occurred as a consequence of alcohol-related health problems, *First Statistical Compendium on Alcohol and Health,* U.S. Department of Health and Human Services (1981). Every indication points to a continued increase in alcohol-related health problems.

One of the major means of reducing the damage due to a pathologic process is early intervention. In this regard, diagnostic tools would have considerable value to the physician. The development of a diagnostic criterion to identify individuals at risk for becoming alcoholic is currently based upon the clear demonstration that genetic factors are important to the development of alcohol-related problems in a significant portion of the alcoholic population, Schuckit, in *Medical and Social Aspects of Alcohol Abuse,* B. Tabakoff et al., (eds.), p. 31, Plenum Press, N.Y. (1983). Thus, gene products which predispose an individual to alcohol-related problems, or closely linked gene products, could be used as "markers" to identify individuals potentially at risk for developing alcohol-related health and social problems. Early identification of "predisposed" individuals could allow primary intervention and prevention efforts to be instituted.

Although substantial work has been directed at exploring biochemical or physiological candidates for "markers," the quest is far from complete. Such studies have included examination of blood groups, Hill et al., J. Stud. Alc. 36:981 (1972), color blindness, Cruze-Coke et al., Lancet 2:1281 (1966), and enzymes related to the metabolism of ethanol, Agarwal et al., Pharmacol. Biochem. Behav. 18(Suppl. 1):89 (1983). These approaches have not proved to be successful. More recently, Schuchkit, Pharmacol. Biochem. Behav. 13(Supp. 1):9 (1980), has reported that sons of alcoholics ("family history-positive" individuals) generate, ethanol-derived blood acetaldehyde levels twice those generated by matched family history-negative individuals. Since these studies have been criticized with regard to methods employed for measurement of acetaldehyde, Eriksson, Science 207:1383 (1980), the utility of this measure must await the resolution of this controversy. Also, Von Knorring et al., Acta Psychiatrica Scandinavia 72:51 (1985) have suggested that platelet monoamine oxidase activity measures could be of value in identifying particular subgroups of alcoholics. However, examination of the presented data casts doubt that monoamine oxidase activity, in and of itself, is a distinguishing parameter for identifying individuals predisposed to alcoholism.

Another test which may distinguish individuals genetically predisposed to alcohol-related problems is the electrophysiologic response of the individuals to external stimuli. Characteristic patterns in auditory and other event-related evoked potentials have been reported in individuals with a positive family history of alcoholism, Elmasian et al., Soc. Neurosci, Abstr. 7:158 (1981), Begleiter et al., Alc.: Clin. Exptl. Res. 6:136 (1982), Begleiter et al., Science 225:1495 (1984). While this is an important finding, the generation of appropriate information regarding evoked potentials requires expensive equipment and personnel with specialized training not generally available to the practicing physician.

SUMMARY OF THE INVENTION

The present invention contemplates a method for identifying a subgroup of individuals likely to be predisposed to alcohol abuse. This method comprises the steps of isolating platelets from an individual's blood, assaying separate portions of the isolated platelets for monoamine oxidase (MAO) and adenylate cyclase (AC) activity, and comparing to one another the relative activities of these two enzymes as present in the platelets. Preferably the adenylate cyclase assay is carried out in the presence of an adehylate cyclase activity stimulating agent such as cesium fluoride, prostaglandin $E_1$ and/or guanylylimidodiphosphate [Gpp(NH)p]. The MAO assay is carried out in the absence and presence of a $C_1$ to $C_4$ aliphatic alcohol which inhibits the MAO activity.

A further aspect of the present invention is an assay for ascertaining individuals likely to be predisposed to alcohol abuse which comprises the steps of: providing an aliquot of blood platelet membranes; dividing the aliquot into two portions; admixing one portion of the aliquot with a predetermined amount of adenosine triphosphate (ATP) to form an admixture; incubating the resulting admixture for a predetermined time period during which adenylate cyclase present in said aliquot reacts with adenosine triphosphate; terminating the reaction of adenylate cyclase, e.g., by boiling, at the end of the incubation period; determining the amount of cyclic adenosine monophosphate produced during the incubation period; admixing the other portion of the aliquot of platelet membranes with a predetermined amount of radioactive phenylethylamine (PEA) to form an admixture; partitioning the PEA-containing mixture into first and second parts; combining a $C_1$ to $C_4$ aliphatic alcohol, such as ethanol, with the first part; thereafter incubating both the first part and the second part for a predetermined time period during which monoamine oxidase in said parts, reacts with phenylethylamine; terminating the reaction of MAO by addition thereto of excess non-radioactive phenylethylamine; determining the amount of deaminated product (phenylacetaldehyde) produced during the incubation period; calculating the inhibition of MAO activity by the added alcohol; and calculating the ratio of the inhibition of MAO activity to the AC activity.

A benefit of the present invention is that individuals likely to be predisposed to alcohol abuse are identified by two easily interpreted assays.

A further benefit of the invention is that the assay uses platelets which are readily obtainable by venipuncture.

Another benefit of the invention is that the two assays measure genetically-determined markers so that individuals can be counseled before, as well as after, they develop a dependence on alcohol.

BRIEF DESCRIPTION OF THE DRAWING

FIG. 1 is a graph of the frequence distribution of the ratio of: percent inhibition of MAO activity by ethanol, divided by cesium fluoride (CsF)-stimulated AC activity, in platelets for each individual alcoholic or recovering alcoholic (individuals who have abstained from alcohol use for 12 or more months). The mean ratio for control individuals is indicated by the lines parallel to the x-axis, indicating the mean ratio of 0.054, one standard deviation from this mean is indicated by the cross-hatched region, and two standard deviations of this mean ratio are indicated by the dotted region. Each data point on the FIGURE represents the calculated value of the ratio for one individual alcoholic or for a recovering alcoholic. The ordinate scale represents the numerical values for the ratio of percent inhibition of MAO activity divided by CsF-stimulated AC activity (picomoles of cyclic AMP formed per minute per milligram of platelet protein).

DETAILED DESCRIPTION

The present invention contemplates a method for selecting individuals likely to be predisposed to alcohol abuse which comprises the following steps. An aliquot of platelet membranes from blood of an individual is isolated and divided into two portions. One portion of the aliquot is assayed for AC activity, and the other portion for MAO activity in the presence and absence of a $C_1$ to $C_4$ aliphatic alcohol, e.g., ethyl alcohol.

In a preferred embodiment, the AC assay step is carried out in the presence of an AC stimulating agent which acts through the stimulatory G-coupling protein (guanine nucleotide-binding protein). Preferred AC stimulating agents are cesium fluoride (CsF), prostaglandin $E_1$ ($PGE_1$), and guanylylimidodiphosphate [Gpp(NH)p]. Most preferred for this purpose is CsF. The MAO assay is carried out in the presence and absence of an alcohol which inihibits the enzyme activity. Most preferred inhibitor is ethyl alcohol.

As discussed in detail hereinfter in *Results*, the combined measurements of MAO activity and AC activity have been found to be a reliable marker for a significant portion of individuals predispoed to alcoholism. Basal, guanylylimidodiphosphate [Gpp(NH)p]-, fluoride- and prostaglandin $E_1$ (PGE)-stimulated AC activities have been found to be generally lower in platelets of alcoholics compared to control subjects and the values remain unchanged even after prolonged abstinence. The absolute values of stimulated AC activities were significantly disminished in platelets of alcoholics in comparison to control subjects. These findings clearly demonstrate a reduction in the amount of platelet AC activity in alcoholics, since platelet counts and amount of protein per platelet of alcoholics and controls were not found to be different. Platelet AC activity remained low in alcoholics who had abstained frcm alcohol for varying lengths of time (up to 24 months). These results indicate that lowered platelet AC activity is an inherent characteristic of alcoholic patients.

Absolute values of platelet MAO activity in alcoholic were not significantly different from those of controls. However, a $C_1$ to $C_4$ aliphatic alcohol, e.g., ethyl alcohol, can be added to the monoamine oxidase assay in vitro to inhibit the enzyme, Tabakoff et al., Psychopharmacol. 87:152 (1985). This inhibition was found to be significantly greater in platelets obtained from alcoholics than from controls. Inhibition of MAO by ethyl alcohol, or like $C_1$ to $C_4$ aliphatic alcohol, remained increased in platelets obtained from alcoholics who had abstained from alcohol for varying lengths of time (up to 24 months). Therefore, the increased sensitivity of platelet MAO to inhibition by alcohol also represents an inherent characteristic of alcoholics.

The predictive value of these inherent differences for identification of individuals predisposed to alcoholism can be enhanced by calculating the ratio of ethanol-inhibited MAO activity to CsF-stimulated AC activity. This ratio then provides a powerful discriminant of a significant subgroup of individuals predisposed to alcoholism. Since inhibition of MAO is greater in alcoholics, while AC activity is lowered, the ratio of these two activities is significantly higher in alcoholics than in non-alcoholic controls. By using a cutoff value of this ratio (i.e., 0.146) which is two standard deviations greater than the mean of control values, at least 57% of the alcoholic population can be distinguished. Using this "cutoff" value, the false positive rate for controls was 0%, and would not be expected to exceed 5% even in an infinitely large population. Assaying platelet AC and MAO acitivities, therefore, provides a reliable discriminator of a substantial portion of alcoholic individuals, and individuals predisposed to alcoholism.

The use of the ratio of inhibition of MAO to CsF-stimulated AC activity as the discriminant value allows for a greater absolute difference in value between alcoholics and controls, and thus a lower porportion of false positives. Studies to date have established the specificity and accuracy of this measure, as well as have developed easily-performed clinical assays of platelet AC and MAO activities described in detail hereinafter in *Methods*.

Results

The description of patients used in the studies is included in Table 1, below.

TABLE 1

| Characteristics of Patients Used in Studies | | |
|---|---|---|
| | Alcoholics and Recovering Alcoholics[1] | Controls |
| Total Number | 146 | 50 |
| Age (Years) | 39 ± 9; 22-64 (range) (n = 117) | 37 ± 11; 24-63 (range) (n = 39) |
| Days Since Last Drink | 19 ± 17; 0-90 (range) (n = 138) | 4 ± 4; 1-30 (range) (n-46) 6 mo (n = 1) 3 yr (n = 2) 20 yr (n = 1) |
| Qty. Alcohol Consumed | 120-500 g/day (n = 146) | Less than 15 g/day (n = 50) |
| Withdrawal Scores* | 0-25 range (n = 47) | 0-5 (n = 43) |
| Anxiety/Depression | 53% Positive (n = 119) | 21% Positive (n = 39) |

TABLE 1-continued

| | Characteristics of Patients Used in Studies | |
|---|---|---|
| | Alcoholics and Recovering Alcoholics[1] | Controls |
| Smoking | 86% Positive (n = 117) | 21% Positive (n = 39) |
| Race | 55% Black/44% Caucasian/ 1% Native American (n = 146) | 72% Caucasian/24% Black/ 4% Oriental (n = 50) |
| Education | 10-15 Years (n = 40) | 12-22 Years (n = 26) |
| Duration of Problems with Alcohol | 14 ± 9 Yrs; 1-38 Yr (range) (n = 100) | 0 (n = 50) |

[1] Recovering alcoholics were Alcoholics Anonymous counselors recruited from the Alcoholics Anonymous chapter of the Chicago VA Westside Medical Center. These individuals had abstained from alcohol for 12 to 24 months.
*Scored as described by M. M. Gross et al. in B. Kissin and H. Begleiter (eds.), The Biology of Alcoholism, Vol. 3, New York, Plenum Press, 1974.
Where applicable, values represent mean ± S.D.
n - Represents the number of individuals on whom accurate data regarding demographic and alcohol related variables was available. All alcoholics satisfied the DSM III criteria for alcoholism.

In platelets of control subjects, the $K_m$ of adenylate cyclase for Mg-adenosine triphosphate (ATP) was determined to be 20.1±3.8 micromoles (uM) (mean±SEM, n=3). This value was obtained using 10 mM $Mg^{++}$ and varying concentrations of ATP, as described in detail hereinafter in *Methods*. The maximal activity of the enzyme under these conditions (i.e., $V_{max}$) was 15.1±2.4 picomoles (pmole) cAMP produced/minute (min)/milligram (mg) protein (mean±SD; n=3). Intraassay variability was determined by assaying basal activity in sextuplicate. The coefficients of variation in two such experiments were 6.2% and 9.9%. To determine interassay variability, basal activity in four aliquots from the same platelet preparation was determined in assays on four separate days within a two-week period. The coefficient of variation was 17.0%. Stability of AC activity in individuals over time was assessed by determining basal and stimulated AC activity in different blood samples from given individuals (controls). The results for blood samples taken at least one week apart are shown in Table 2, below.

TABLE 2

| Platelet Adenylate Cyclase Activities In Repeated Blood Samples from the Same Subject | | | | |
|---|---|---|---|---|
| Patient | Sample 1 | Sample 2 | Sample 3 | Mean ± SD |
| Adenylate Cyclase Activity - Basal | | | | |
| No. 5 | 12.9 | 13.0 | 14.6 | 13.5 ± 1.0 |
| No. 6 | 20.1 | 23.6 | 19.1 | 20.9 ± 2.4 |
| Adenylate Cyclase Activity - CsF-Stimulated | | | | |
| No. 5 | 83.6 | 69.5 | 72.3 | 75.1 ± 7.5 |
| No. 6 | 104.2 | 98.0 | 100.2 | 100.8 ± 3.1 |

Blood was drawn from these control subjects at intervals of one week.

The means values for basal, PGE-stimulated, Gpp(NH)p-stimulated and cesium fluoride (CsF)-stimulated AC activity in the population of controls, alcoholics and recovering alcoholics are shown in Table 3, below.

TABLE 3

| Adenylate Cyclase Activity in Platelets of Control Subjects and Alcoholics | | | | |
|---|---|---|---|---|
| | Enzyme Activity (pmole cAMP/mg protein/minute) | | | |
| | Basal | +CsF (uM) | +Gpp(NH)p (1 uM) | +PGE₁ |
| Controls | 14.9 ± 3.7 (49) | 97.9 ± 28.7 (49) | 50.4 ± 15.0 (36) | 115.5 ± 32.9 (21) |
| Alcoholics | 13.9 ± 6.0 | 78.2 ± 27.8* | 37.8 ± 14.4* (43) | 84.4 ± 36.1* (34) |
| Recovering Alcoholics | 12.9 ± 5.6* (38) | 70.6 ± 27.2* (38) | 37.2 ± 16.5* (23) | 42.7 ± 12.8*# (8) |

AC activity was measured in membranes of platelets obtained from controls, alcoholics and recovering alcoholics, as described in the text. Values represent mean ± SD of the number of samples indicated in parentheses.
*p 0.05, compared to control values (ANOVA and Tukey-Kramer test).
p 0.05, compared to alcoholic values (ANOVA and Tukey-Kramer test).

Sodium ion was not included in these assays (e.g., NaF) since Na⁺ inhibits stimulation of platelet AC activity, Jakobs et al., J. Recep. Res. 4:443-458, 1984. The data from a relatively large number of alcoholic and control patients demonstrate that stimulated AC activities are significantly lower in platelets of alcoholics as compared to controls. It is also interesting that the basal, as well as stimulated AC activities in platelets of recovering alcoholics are significantly lower than those of controls. Since the recovering alcoholics had abstained from alcohol for more than 12 months, the observed differences are believed to reflect an inherent characteristic of the alcoholic group of patients.

Since basal as well as stimulated AC activities were decreased in the alcoholics, the fold stimulation over basal caused by fluoride, Gpp(NH)p or PGE, did not appear to vary among groups. This finding indicates that the change in platelet AC activity in alcoholics reflects a decreased amount of AC or the stimulatory coupling protein, rather than altered kinetic properties. Although the data are reported herein on the basis of platelet protein content, no difference was found in the platelet count or platelet protein between our alcoholics and controls. Thus, the decreased levels of platelet AC activity in the alcoholics are not simply a result of changes in protein content or platelet concentration.

In platelets of control subjects, the $K_m$ of MAO for PEA was 1.4±0.2 uM (mean±SEM, n=6). This value was obtained using varying concentration of PEA, as described hereinafter in *Methods*. The maximal activity ($V_{max}$) of the enzyme under these conditions was 508±37 pmole/mg protein/minute (n=4). The $K_i$ value for ethyl alcohol inhibition of platelet MAO activity, when PEA was used as substrate, was 167±54 mM (mean±SEM, n=4). Inhibition by ethyl alcohol added in vitro was reversible and was "competitive" in nature (i.e., the amount of inhibition depended on the concentration of substrate). Intraassay variability for MAO was determined by measuring activity under identical conditions in eight assay tubes. The coefficient of variation was 3.5% in the absence of ethyl alcohol, and 6.3% in the presence of 400 mM ethyl alcohol. Stability of MAO activity, and inhibition by ethyl alcohol, in individuals over time was assessed by measuring activity in different blood samples from given individuals. The results are shown in Table 4, below.

TABLE 4

Platelet Monoamine Oxidase Activities in Repeated Blood Samples

| Patient | Sample 1 | Sample 2 | Sample 3 | Mean ± SD |
|---|---|---|---|---|
| MAO Activity Using PEA as Substrate (pmole product/mg protein/min)[1] | | | | |
| No. 1 | 483 | 488 | 405 | 459 ± 47 |
| No. 2 | 157 | 167 | 169 | 164 ± 16 |
| Percent Inhibition by 400 mM Ethyl Alcohol | | | | |
| No. 1 | 7.0 | 7.6 | 6.1 | 6.9 ± 0.8 |
| No. 2 | 13.1 | 7.9 | 9.8 | 10.3 ± 2.6 |
| MAO Activity Using Dimethylaminobenzylamine (DAB) as Substrate (pmole product/mg protein/min)[2] | | | | |
| No. 3 | 86.6 | 83.8 | 105.7 | 92.0 ± 11.9 |
| No. 4 | 147.6 | 136.5 | 123.2 | 135.8 ± 12.2 |
| No. 5 | 158.7 | 163.4 | 194.2 | 172.1 ± 19.3 |
| No. 6 | 135.9 | 129.2 | 116.4 | 127.2 ± 9.9 |

[1] MAO activity was assayed using 12 uM PEA as substrate. The first platelet sample provided a baseline value. The second and third samples were drawn five and six days later.
[2] MAO activity was also assayed using 5 mM DAB as substrate, Tabakoff et al., Psychopharmacol. 87:1526 (1985). Blood was drawn from control subjects at intervals of one week.

The mean values for MAO activity and for percent inhibition by ethanol in the population of alcoholics, recovering alcoholics and controls are shown in Table 5, below. The mean values of MAO activity in the absence of ethanol in the assay did not differ significantly among the three groups. However, the data demonstrate that inhibition of MAO activity by ethanol was significantly greater in platelets of alcoholics and recovering alcoholics than controls. Since this inhibition did not appear to return toward control values in the recovering alcoholics, the increased sensitivity to ethanol inhibition was taken to reflect an inherent characteristic of platelets of alcoholics. It has been postulated that ethanol inhibition of platelet MAO activity involves perturbation of membrane lipids surrounding the enzyme, Tabakoff, et al., Psychopharmacol. 87:152, 1985. The differences between control and alcoholic populations may result from different characteristics of the platelet membranes.

TABLE 5

Monoamine Oxidase Activity in Platelets of Alcoholics.

| | MAO Activity[1] (pmole product/mg protein/min) | Percent Inhibition by 400 mM ETOH |
|---|---|---|
| Controls | 377.2 ± 158.5 (28) | 7.5 ± 6.9 (28) |
| Alcoholics | 445.1 ± 241.1 (56) | 12.6 ± 7.0 (54)** |
| Recovering Alcoholics | 458.2 ± 153.7 (22) | 11.4 ± 6.2 (22)* |

[1] MAO Activity was measured using 12 uM PEA as substrate. Values represent mean ± SD of the number of samples indicated in parentheses.
**P < 0.01,
*P < 0.05 compared to control value (Student's t-test).

An analysis of various correlates of alcoholism that might be associated with lowered platelet AC activity revealed no significant correlation of AC activity with duration of alcohol problems (r=0.034), withdrawal severity (r=0.30), or times since last drink (r=0.26). In addition, there did not appear to be an association between smoking or ethnic origin and platelet AC activity. The intensity of inhibition of MAO activity by ethanol was also not significantly correlated with duration of alcohol problems (r=0.127) or times since last drink (r=0.061). There did not appear to be an association between smoking or ethnic origin and sensitivity of platelet MAO activity to inhibition by ethanol. These analyses support the conclusion that low platelet AC activity and enhanced sensitivity of platelet MAO to inhibition by ethanol are intrinsic characteristics of the alcoholic population.

A plot of individual values of the ratio of percent inhibition of MAO activity divided by CsF-stimulated AC activity demonstrates the differences between the majority of alcoholic individuals and the control group. The mean ±S.D. for such ratios for controls was 0.054±0.046, for alcoholics it was 0.183±0.135 and for recovering alcoholics it was 0.126±0.07. Using this ratio, 57% of alcoholics were found to have values more than two standard deviations higher than the control mean. If a cutoff value of one standard deviation is used, 70% of alcoholics can be identified, with 11% of controls showing false positive values.

Overall, the data indicated that measurements of platelet AC activity, in particular CsF-stimulated AC activity, in combination with determinations of ethanol inhibition of platelet MAO activity, are useful as a marker for distinguishing a substantial portion of individuals predisposed to alcohol abuse. As shown in the FIGURE, ratio values for control individuals fall primarily in the ranges of 0-0.1, while the majority of alcoholics have significantly higher ratio values, due to lower AC activity and increased sensitivity of platelet MAO to in vitro inhibition by ethanol.

METHODS

Preparation of Platelet Membranes

Platelets were prepared from whole blood (20 ml) which was obtained by venipuncture from healthy volunteers and alcoholic subjects. After standing at room temperature for approximately three to four hours in citrate-phosphate-dextrose solution, each blood sample was centrifuged at 180×G for two minutes. The platelet-rich plasma (PRP) was carefully removed and platelet count was determined from aliquots (20 ul) of the PRP with a Coulter S-plus Thrombocounter. The PRP was centrifuged at 16,000 g for ten minutes. The pellet was resuspended in 50 ml of cold 50 mM Tris-HCl, pH 7.5, containing 150 ml NaCl and 20 mM ethylene diamine tetraacetic acid (EDTA). The centrifugation was repeated twice, and the final pellet was resuspended in 1 ml of cold 5 mM Tris-HCl, pH 7.5, containing 5 mM EDTA. Suspensions were rapidly frozen at −70° C., and samples were stored at −70° C. for no longer than four weeks prior to assay.

AC Assay

AC activity was assayed by a modification of previously described methods, Hoffman and Tabakoff, J. Pharmacol. Exptl. Ther. 208:216 (1979); Luthin and Tabakoff, Pharmacol Exptl. Ther., 288:579 (1984). Platelets were thawed at room temperature, aliquots of platelets were diluted to 4 ml with 5 mM Tris-HCl buffer containing 5 mM EDTA, and the suspension was centrifuged at 39,000×G for ten minutes at 4° C. The platelet pellet was then resuspended in assay buffer with no ATP added (25 mM Tris-maleate, pH 7.4, 10 mM theophylline, 10 mM $MgCl_2$, 0.2 mM EDTA) at a concentration of 1.5-2.5 mg of protein/ml. AC activity was measured in a final assay volume of 0.5 ml. The reaction mixture contained assay buffer described above and 0.25 mM $^{32}$p-ATP (approximately $3 \times 10^6$ cpm per assay tube). Gpp(NH)p (10 uM), CsF (10 mM) or prostaglandin $E_1$ (PGE) (1 uM) were added to assay tubes as appropriate. Reactions were initiated by addition of platelet membranes (50 ul) following a three-minute incubation period, and were continued for ten minutes at 30° C. The reaction was stopped by placing the tubes in a boiling water bath for three minutes. Tubes were placed on ice and 0.5 ml of stop solution (8 mM ATP; 0.28 mM cAMP) was added to each tube. The $^{32}$p-cAMP was isolated by sequential chromatography on Dowex (Sigma Chemical Co., St. Louis, Mo.) and alumina columns (Sigma Chemical Co., St. Louis, Mo.), Salomon et. al., Anal. Chem. 58:541, (1974). To each column effluent, 10 ml of scintillation cocktail was added, and $^{32}$p-cAMP was quantitated in a liquid scintillation spectrometer. All values were corrected for percentage recovery of the product ($^{32}$p-cAMP).

MAO Assay

To measure the deamination of $^{14}$C-PEA, assay mixtures (total volume, 0.3 ml) contained approximately 15 ug of platelet protein. Reactions were carried out in 0.1 M sodium phosphate, pH 7.4, at 37° C. A five-minute preincubation period preceded the addition of substrate, and blanks were preincubated in the presence of $1 \times 10^{-3}$ M pargyline. Appropriate concentrations of $^{14}$C-PEA (10,000 dpm per nmole) were added to initiate the reaction, and the incubation was carried out for 15 minutes. The reaction was stopped by placing the tubes in an ice bath and adding 1.0 ml of ice-cold unlabeled PEA solution ($10^{-4}$ M) to each assay tube. A 1-ml aliquot was then removed from each tube and placed on an Amberlite TM ion exchange column, Tabakoff et. al., Psychopharmacol. 87:152 (1985). The columns were washed with two 1-ml portions of distilled water and the effluent was collected in scintillation vials. Two additional ml of water and 20 ml of scintillation fluid were added to each vial, and radioactivity was determined in a liquid scintillation spectrometer. To study the effects of ethanol or other alcohols on MAO activity, the alcohols were added to incubation mixtures five minutes prior to the addition of substrate.

The foregoing specification and the examples are intended as illustrative of the present invention and are not to be taken as limiting. Still other variations within the spirit and scope of this invention are possible and will readily present themselves to one skilled in the art.

What is claimed is:

1. A method for determining predisposition toward alcoholism by ascertaining the relative adenylate cyclase and monoamine oxidase activities of platelets from an individual which comprises the steps of:
   isolating platelets from blood of the individual;
   assaying said platelets for adenylate cyclase and monoamine oxidase activities; and
   and comparing said activities by determining the ratio thereof.

2. The method in accordance with claim 1 wherein the adenylate cyclase assaying step is carried out in the presence of an adenylate cyclase activity stimulating agent.

3. The method in accordance with claim 2 wherein the adenylate cyclase activity stimulating agent is a member of the group consisting of cesium fluoride, prostaglandin E, and guanylylimidodiphosphate.

4. The method in accordance with claim 2 wherein the adenylate cyclase activity stimulating agent is cesium fluoride.

5. The method in accordance with claim 2 wherein the adenylate cyclase activity stimulating agent is prostaglandin $E_1$.

6. The method in accordance with claim 2 wherein the adenylate cyclase stimulating agent is guanylylimidodiphosphate.

7. The method in accordance with claim 1 wherein the monoamine oxidase assaying step is carried out in the presence of a monoamine oxidase inhibiting agent.

8. The method in accordance with claim 7 wherein the monoamine oxidase inhibiting agent is a $C_1$ to $C_4$ aliphatic alcohol.

9. The method in accordance with claim 8 wherein the monoamine oxidase inhibiting agent is ethyl alcohol.

10. An assay for ascertaining individuals likely to be predisposed to alcohol abuse as a result of a high ratio of monoamine oxidase inhibiting activity to adenine cyclase activity which comprises the steps of:
    providing an aliquot of blood platelet membranes;
    admixing one portion of said aliquot with a predetermined amount of adenosine triphosphate to form an admixture;
    incubating the resulting adenosine triphosphate-containing admixture for a predetermined time period during which adenylate cyclase present in said one portion reacts with adenosine triphosphate;
    terminating the reaction of adenylate cyclase at the end of the incubation period; and
    determining the amount of cyclic adenosine monophosate produced during the incubation period;
    admixing another portion of said aliquot with a predetermined amount of phenylethylamine to form a phenylethylamine-containing admixture;
    partitioning the obtained phenylenethylamine-containing admixture into first and second parts;
    combining a $C_1$ to $C_4$ aliphatic alcohol with the first part;
    incubating both the first and second part for a predetermined time period during which monoamine oxidase present in each of said first and second part reacts with phenylethylamine;
    terminating the reaction of monoamine oxidase at the end of the incubation period;
    determining the amount of phenylacetaldehyde produced during the incubation period;
    calculating the inhibition of monoamine oxidase activity by the alcohol present in the first part of the phenylethylamine-containing admixture; and
    calculating the ratio of the inhibition of MAO activity to the adenylate cyclase activity.

11. The assay in accordance with claim 10 wherein the aliphatic alcohol is ethyl alcohol.

* * * * *

UNITED STATES PATENT AND TRADEMARK OFFICE
CERTIFICATE OF CORRECTION

PATENT NO. : 4,770,996

DATED : September 13, 1988

INVENTOR(S) : Boris Tabakoff

It is certified that error appears in the above-identified patent and that said Letters Patent is hereby corrected as shown below:

Col. 2, line 22, "adehylate" should be -- adenylate --.
Col. 3, line 4, "ratio" should be -- ratio --.
Col. 4, line 24, "ratio" should be -- ratio --.
Col. 5, line 53, "means" should be -- mean --.
Cols. 5 and 6, Table 3, in the heading for the third column, "+CsF uM)" should be -- +CsF (10 mM) --.
Cols. 5 and 6, Table 3, in the heading for the fourth column, "+Gpp(NH)p (1 uM)" should be -- +Gpp(NH)p (10uM) --.
Cols. 5 and 6, Table 3, in the heading for the fifth column, "+PGE$_1$" should be -- +PGE$_1$ (1uM) --.
Col. 9, line 43, "Amberlite TM" should be -- Amberlite$^{TM}$ --.
Col. 10, line 47, "phenylenethylamine" should be -- phenylethylamine --.

Signed and Sealed this

Ninth Day of May, 1989

Attest:

DONALD J. QUIGG

Attesting Officer

Commissioner of Patents and Trademarks